United States Patent
Ashmole et al.

(10) Patent No.: US 9,633,482 B2
(45) Date of Patent: Apr. 25, 2017

(54) APPARATUS AND METHOD FOR RESTRICTING IMAGE DATA VISUALIZATION

(71) Applicant: Toshiba Medical Systems Corporation, Otawara-shi (JP)

(72) Inventors: Dominic Ashmole, Edinburgh (GB); Andrew Smout, Edinburgh (GB)

(73) Assignee: Toshiba Medical Systems Corporation, Otawara-shi (JP)

( * ) Notice: Subject to any disclaimer, the term of this patent is extended or adjusted under 35 U.S.C. 154(b) by 138 days.

(21) Appl. No.: 14/457,221

(22) Filed: Aug. 12, 2014

(65) Prior Publication Data
US 2016/0048944 A1 Feb. 18, 2016

(51) Int. Cl.
| | | |
|---|---|---|
| G06T 7/00 | (2006.01) |
| G06T 19/20 | (2011.01) |
| A61B 6/03 | (2006.01) |
| G06F 19/00 | (2011.01) |
| G06F 21/62 | (2013.01) |
| A61B 6/00 | (2006.01) |

(52) U.S. Cl.
CPC .............. *G06T 19/20* (2013.01); *A61B 6/032* (2013.01); *A61B 6/5211* (2013.01); *G06F 19/321* (2013.01); *G06F 21/6245* (2013.01); *G06T 7/0042* (2013.01); *A61B 6/5252* (2013.01); *G06T 2207/10081* (2013.01); *G06T 2207/10088* (2013.01); *G06T 2207/30004* (2013.01); *G06T 2207/30196* (2013.01); *G06T 2210/41* (2013.01); *G06T 2219/2012* (2013.01)

(58) Field of Classification Search
CPC .. G06F 21/6245; G06F 19/321; G06F 19/322; G06K 9/3241; G06T 2207/10081
See application file for complete search history.

(56) References Cited

U.S. PATENT DOCUMENTS

| 7,202,808 | B2 | 4/2007 | Fleisher et al. | |
|---|---|---|---|---|
| 7,519,591 | B2 | 4/2009 | Landi et al. | |
| 2006/0262902 | A1* | 11/2006 | Wattenburg | G01N 23/04 378/57 |
| 2009/0169074 | A1* | 7/2009 | Avinash | G06F 19/321 382/128 |

OTHER PUBLICATIONS

Cai, Yang; Pavlyshak, Iryna; Laws, Joseph; Magargle, Ryan and Hoburg, James, "Augmented Privacy with Virtual Humans", year="2008", pp. ="176-193".*

X. X Q. Zhou, H. K. Huang and S. L. Lou, "Authenticity and integrity of digital mammography images," in IEEE Transactions on Medical Imaging, vol. 20, No. 8, pp. 784-791, Aug. 2001. doi: 10.1109/42.938246.*

(Continued)

*Primary Examiner* — Utpal Shah
(74) *Attorney, Agent, or Firm* — Oblon, McClelland, Maier & Neustadt, L.L.P.

(57) ABSTRACT

An image processing apparatus comprises a data receiving unit for receiving a medical image data set, the medical image data set being representative of at least part of a patient, and a processing unit for processing the medical image data set to restrict visualization of at least part of the patient's skin surface.

19 Claims, 4 Drawing Sheets

(56) References Cited

OTHER PUBLICATIONS

Joseph Laws, Nathaniel Bauernfeind, and Yang Cai. 2006. Feature hiding in 3D human body scans. Information Visualization 5, 4 (Dec. 2006), 271-278.*

Xiangrong Zhou ; Takeshi Hara ; Hiroshi Fujita ; Ryujiro Yokoyama ; Takuji Kiryu ; Hiroaki Hoshi; Automated segmentations of skin, soft-tissue, and skeleton, from torso CT images. Proc. SPIE 5370, Medical Imaging 2004: Image Processing, 1634 (May 12, 2004).*

"I've got an idea and it's not pants! The X-ray proof underwear that protects air passenger's modesty" Daily Mail Reporter, http://www.dailymail.co.uk/sciencetech/article-1366421/X-ray-proof-underwear-protects-air-passengers-modesty-body-scanners.html, Mar. 2011, 4 pages.

"Welcome to Medical Patient Modesty" http://www.patientmodesty.org/, Jul. 2014, 2 pages.

Maurice Bernstein, M.D., "Bioethics Discussion Blog" http://bioethicsdiscussion.blogspot.co.uk/search?q=modesty, Aug. 2014, 228 pages.

Jennifer Golson, et al., "Muslim woman sues Somerset Medical Center for religious discrimination" http://www.nj.com/news/index:ssf/2010/07/muslim_woman_sues_somerset_hos.html, Jul. 2010, 5 pages.

Mohammad A. Dabbah, et al., "Detection and location of 127 anatomical landmarks in diverse CT datasets" Medical Imaging 2014: Image Processing, vol. 9034, Mar. 2014, 11 pages.

Antonio Criminisi, et al., "Regression Forests for Efficient Anatomy Detection and Localization in CT Studies" Medical Computer Vision Recognition Techniques and Applications in Medical Imaging, vol. 6533, 2011, pp. 106-117.

René Donner, et al., "Global localization of 3D anatomical structures by pre-filtered Hough Forests and discrete optimization" Medical Image Analysis, vol. 17, No. 8, 2013, pp. 1304-1314.

David Liu, et al., "Anatomical Landmark Detection Using Nearest Neighbor Matching and Submodular Optimization" Medical Image computing and computer-assisted intervention (MICCAI), vol. 7512, 2012, pp. 393-401.

* cited by examiner

APPARATUS AND METHOD FOR RESTRICTING IMAGE DATA VISUALIZATION

FIELD

Embodiments described herein relate generally to a method of, and apparatus for restricting the visualization of certain medical image data. Embodiments have particular application to restricting visualization of at least part of a patient's skin surface.

BACKGROUND

Modern volumetric imaging modalities may produce body images that are almost photo-realistic. Rendering techniques allow selected internal anatomy or pathology to be shown, but are also capable of rendering the skin surface. For example, computed tomography (CT) and magnetic resonance imaging (MRI) acquisitions can be rendered to produce highly realistic 3D images of the human body.

Although volumetric modalities enable excellent visualization of the skin surface, such visualization may not be clinically necessary in some cases. The purpose of a scan may more commonly relate to internal anatomy. In some such cases, visualization of the skin surface may be used for navigation purposes so that a user can navigate to particular body areas. However, navigation may not require a highly accurate representation of the skin surface.

Patient images produced from volumetric imaging modalities may be distributed in a variety of situations (as volumetric image data or as rendered images). Patient images may be distributed to clinicians, for example to referring clinicians or surgeons. Patient images may be displayed at multi-disciplinary team and case conference meetings. Patient images may be displayed in consultations with the patient and/or his or her family members. Patient images may be shown at professional or academic conferences.

The use of forensic CT images is also increasing. Forensic CT refers to CT that is carried out post-mortem. Forensic CT images may relate, for example, to victims of violent crime or deceased soldiers. Forensic CT images may be presented during court or other proceedings, in which case forensic CT images may be presented in front of, for example, the family of the CT subject. The presence of identifying features, for example facial features, in forensic CT images may cause distress.

In the USA, HIPAA (Health Insurance Portability and Accountability Act) requires that patient files be made anonymous before being distributed, including removal of 'full-face photographs and any comparable images'. However, HIPAA does not address the use of volumetric imaging modalities in this context.

In the healthcare context, some groups are concerned about patient modesty issues, and may be dissatisfied with current levels of modesty in healthcare settings. Such groups could be dissatisfied if they were aware of the resolution and realism of imaging that is possible using modern volumetric imaging modalities. The display or distribution of images that include culturally sensitive areas (for example, breast, pelvis or genitals) may be of particular concern to such groups. Specific cultural and religious issues also exist. A patient's dissatisfaction with available levels of modesty may in some circumstances lead to delayed or omitted medical care, lawsuits, or general mistrust of the medical profession.

Some hospitals and clinics may publicize their consideration of patient modesty. During hospital examinations and procedures, efforts may be made to minimize periods of nudity and to provide some patient choice, for example choice of the gender of the clinician attending the patient. Nonetheless, some patients believe they are not treated with respect. Some patients claim that, in some cases, live video streams from the operating room or other images are used for training of students, and the unauthorized use of such images can be of particular concern to some patients.

Any area for which privacy or identification concerns exist (for example, the face) or any area for which modesty concerns exist (for example, breast, pelvis or genitals or other culturally sensitive areas such as upper arm, thigh or shoulder) may be referred to as a sensitive area.

BRIEF DESCRIPTION OF THE DRAWINGS

Embodiments are now described, by way of non-limiting example, and are illustrated in the following figures, in which.

DETAILED DESCRIPTION

Certain embodiments provide an image processing apparatus comprising a data receiving unit for receiving a medical image data set, the medical image being representative of at least part of a patient, and a processing unit for processing the medical image data set to restrict visualization of at least part of the patient's skin surface.

Certain embodiments provide an image processing method comprising receiving a medical image data set, the medical image being representative of at least part of a patient, and processing the medical image data set to restrict visualization of at least part of the patient's skin surface.

Figure 1:
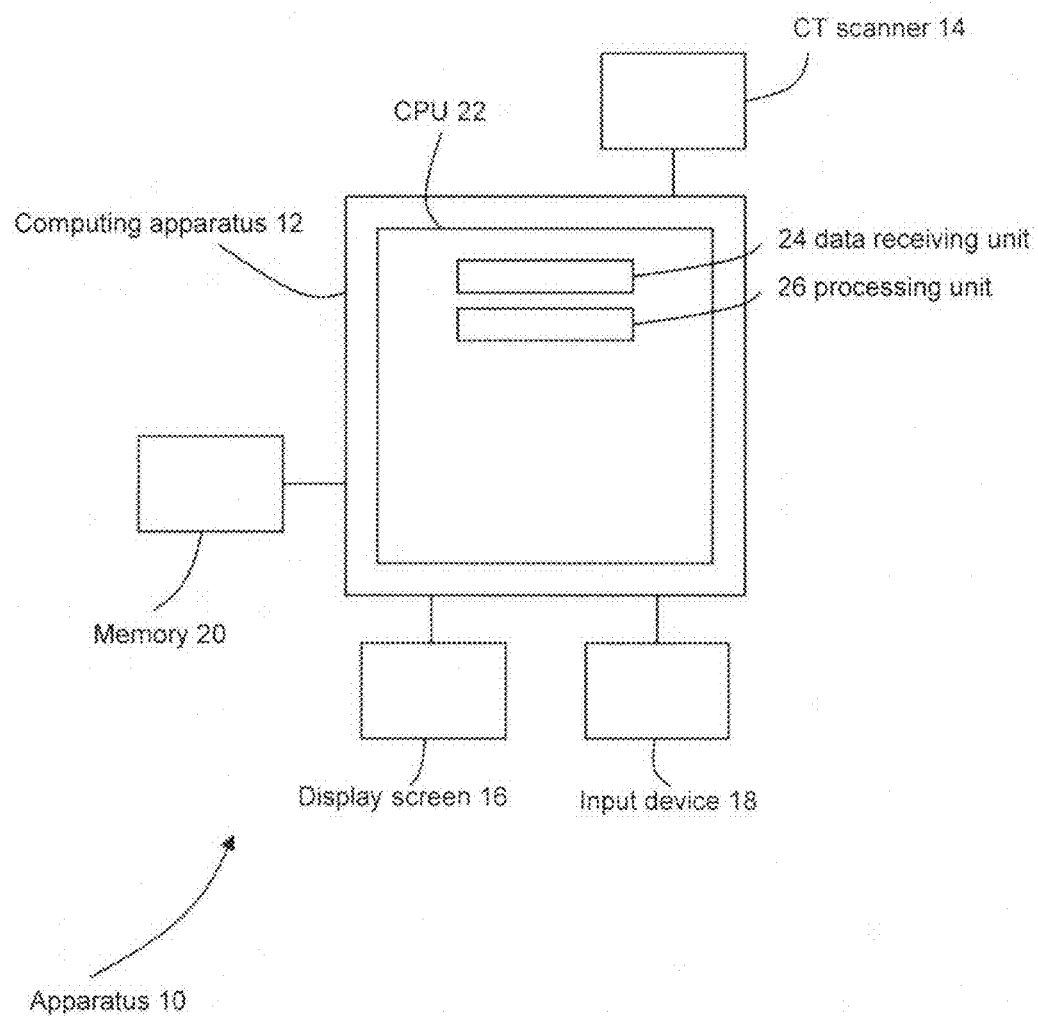
FIG. 1 is a schematic diagram of an image data processing system according to an embodiment.

An image processing apparatus 10 according to an embodiment is illustrated schematically in FIG. 1.

The image processing apparatus 10 comprises a computing apparatus 12, in this case a personal computer (PC) or workstation, which is connected to a CT scanner 14, a display screen 16 and an input device or devices 18, such as a computer keyboard and mouse. In the present embodiment, sets of image data are obtained by the CT scanner 14 and stored in memory unit 20. In alternative embodiments, the image processing apparatus 10 is integrated with the CT scanner. In other embodiments, the image processing apparatus 10 is remote from the CT scanner and image data is transferred between the scanner and image processing apparatus 10 over a network or using physical storage media. In some embodiments, the image processing apparatus 10 is a dedicated apparatus for medical image viewing.

Computing apparatus 12 provides a processing resource for receiving, processing and rendering medical image data. Computing apparatus 12 comprises a central processing unit (CPU) 22 that is operable to load and execute a variety of software modules or other software components that are configured to perform the method that is described below with reference to FIG. 2. In other embodiments, computing apparatus 12 comprises software modules or components that are configured to perform the method that is described below with reference to FIG. 4, or the method of any one or more of the additional embodiments described below.

The computing apparatus 12 includes a data receiving unit 24 for receiving medical image data sets from CT scanner 14, from memory 20 or from a remote data store, and a processing unit 26 for processing the medical image data sets.

In the present embodiment, the data receiving unit 24 and processing unit 26 are each implemented in computing apparatus 12 by means of a computer program having computer-readable instructions that are executable to perform the method of the embodiment. However, in other embodiments, each unit may be implemented in software, in hardware, or in any suitable combination of hardware and software. In some embodiment, the various units may be implemented as one or more ASICs (application specific integrated circuits) or FPGAs (field programmable gate arrays).

The computing apparatus 12 also includes a hard drive and other components of a PC including RAM, ROM, a data bus, an operating system including various device drivers, and hardware devices including a graphics card. Such components are not shown in FIG. 1 for clarity.

Figure 2:
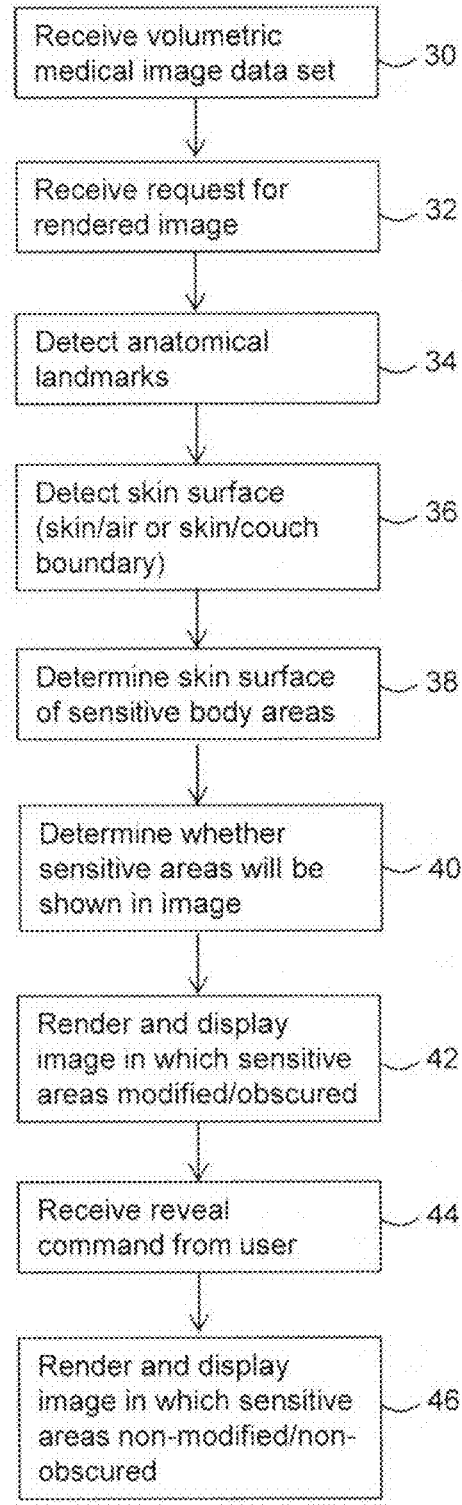
FIG. 2 is a flowchart illustrating in overview a mode of operation of an embodiment.

The system of FIG. 1 is configured to perform a series of stages as illustrated in overview in the flow chart of FIG. 2, in order to render an image in which skin surface regions corresponding to sensitive areas are obscured or modified (the obscuration or modification being reversible by a user in this case).

At stage 30 of FIG. 2, the data receiving unit 24 receives from a memory store 20 a volumetric medical image data set obtained from a CT scan of a patient. The image data set may be part of a series of DICOM (Digital Imaging and Communications in Medicine) files. In further embodiments, the data receiving unit 24 receives the image data set from the CT scanner directly. In other embodiments, the data receiving unit 24 receives the image data set from a remote data store, for example from a server which may form part of a Picture Archiving and Communication System (PACS).

The image data set comprises a three-dimensional array of voxels each representing a property of a corresponding measurement volume. In a CT data set, each voxel usually represents the attenuation of X-ray radiation by a respective, corresponding measurement volume.

In the present embodiment, the image data set was obtained from a CT scan taken using CT scanner 14, which is connected to image processing apparatus 10. In alternative embodiments, the CT scan is taken using any CT scanner. In other embodiments, the image data set comprises data obtained from any radiological scanner that produces volumetric radiological data in any modality, for example CT, MR or ultrasound.

At stage 32, the data receiving unit 24 receives a request for an image to be rendered from the image data set using a skin surface preset. A preset may be a set of three-dimensional rendering parameters suitable for three-dimensional rendering of the image data set. A skin surface preset may be a set of such parameters that renders the image data set such that the skin surface is visible.

Although in the present embodiment, a skin surface preset is requested, in other embodiments, other methods of determining rendering parameters may be used. For example, a method may be used in which rendering parameters are altered such that the skin surface is displayed. In some embodiments, rendering parameters are represented as a color-opacity table and the user may modify the color-opacity table, for example by dragging on a histogram or graph in a user interface, or by using a mouse tool to indirectly modify the table.

In the present embodiment, the request is received as a user input using input device 18. In other embodiments, the request is received automatically without user input. For example, in some embodiments, when an image data set is loaded at stage 30, a request is generated to render one or more standard views of the image data set (for example, an upright anterior shaded volume rendering).

Figure 3:
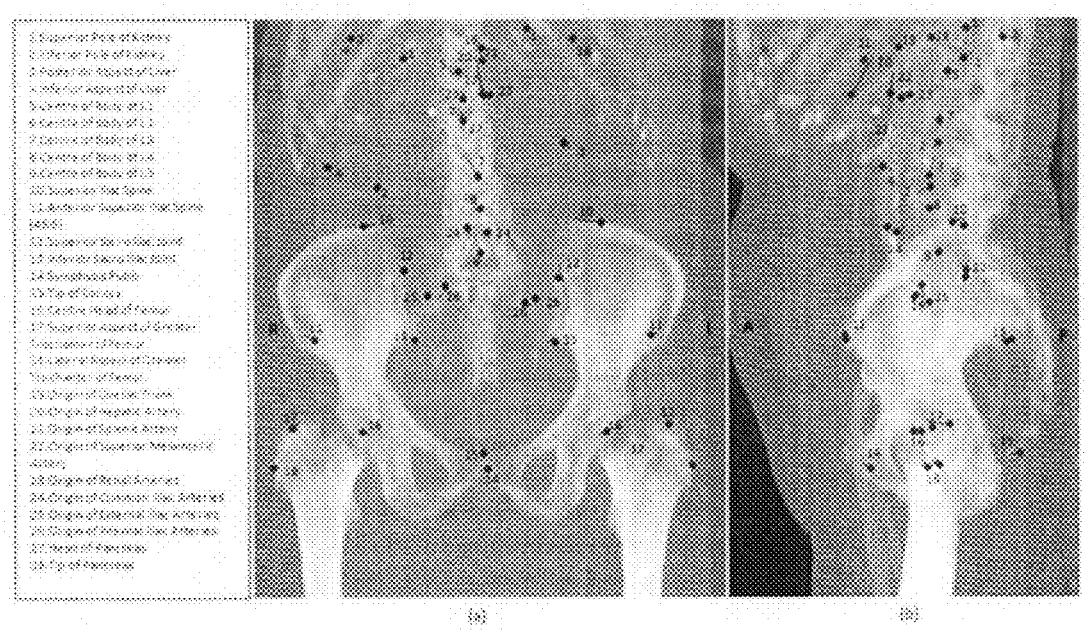
FIG. 3 is an illustration of the positioning of anatomical landmarks on a medical image.

At stage 34, the data receiving unit 24 passes the image data set and details of the render request to the processing unit 26. The processing unit 26 in this case automatically detects and localizes a plurality of anatomical landmarks in the image data set. Anatomical landmarks are recognizable points within the body's structure. Examples of anatomical landmarks include points such as the center of the head of the femur, and the origin of the hepatic artery. Examples of anatomical landmarks are illustrated in FIG. 3.

In the present embodiment, 127 anatomical landmarks are defined in the human body. In the present embodiment, the processing unit 26 detects and localizes in the image data set any of the 127 anatomical landmarks that are present in the image.

In other embodiments, a subset of landmarks is defined which comprises a set of landmarks that is required to determine skin surface regions that correspond to a set of sensitive areas (the process of locating skin surface regions is described below at stage 38) and the processing unit 26 detects and localizes in the image data only the subset of landmarks. For example, if the relevant sensitive areas do not include the face, it may not be necessary to detect anatomical landmarks that are part of the head. Furthermore, in some scans, only a subset of the anatomical landmarks are present (for example in a scan of the head only, or in a scan of the torso only).

Each of the anatomical landmarks that is present in the image data set is detected and localized. In the present embodiment, three-dimensional coordinates representative of the position of each detected and localized anatomical landmark are stored by the processing unit 26.

Although in the present embodiment, landmarks are detected each time the process of FIG. 2 is performed, in other embodiments anatomical landmarks are defined as a once-only step before any request is made to render an image from the image data set. For example, in some cases anatomical landmarks may always be detected as a pre-processing step. Landmark positions may be stored within a CT study. In such cases, the locations of the anatomical landmarks are loaded at stage 34.

In the present embodiment, the processing unit 26 detects the anatomical landmarks automatically using classifiers. Detection and localization of pre-defined anatomical landmarks in medical image data is performed by a classification forest which uses simple image features (see Dabbah et al, Detection and location of 127 anatomical landmarks in diverse CT datasets, *Proc. SPIE* 9034, *Medical Imaging 2014; Image Processing*, 903415, 21 Mar. 2014). Detection results are refined with reference to the spatial relationship between the landmarks.

In other embodiments, other methods of automatic landmark detection may be used. Methods of landmark detection may be as described in, for example, Criminisi, Shotton, Robertson and Konukoglu (2011), 'Regression forests for efficient anatomy detection and localization in CT studies', *Medical Computer Vision. Recognition Techniques and Applications in Medical Imaging*, 106-117; Donner, Menze, Bichof and Langs (2013), 'Global localization of 3D anatomical structures by pre-filtered Hough forests and discrete optimization', *Medical Image Analysis*, 17(8), 1304-1314, doi:10.1016/j.media.2013.02.004; or Liu and Zhou, 'Anatomical landmark detection using nearest neighbor matching and submodular optimization', *Medical image computing and computer-assisted intervention* (MICCAI), 7512, 393-401. In further embodiments, manual or semi-automatic landmark detection methods may be used.

At stage 36, the processing unit 26 detects the skin surface in the image data set by finding the skin/couch boundary at the parts of the scan where the patient's body contacts the couch, and the skin/air boundary at other parts of the scan. The skin surface may be detected by finding areas in which there is high contrast between the Hounsfield Unit (HU) intensity values of adjacent voxels. Boundary detection may be performed in accordance with methods described, for example, in US Patent Application 2012/0219198. In other embodiments, any suitable method of detecting the skin surface may be used.

At stage 38, the processing unit 26 uses the anatomical landmark positions determined in stage 34 and the skin surface determined in stage 36 to define skin surface regions that correspond to sensitive areas of the patient.

In the present embodiment, the processing unit 26 uses a definition of each skin surface region that comprises a boundary for that region that is defined on a generic human body with reference to the anatomical landmarks and skin surface. The processing unit 26 determines, for each skin surface region, where an equivalent boundary for the skin surface region lies in the image data set (which is representative of a particular patient).

In the present embodiment, one or more planes are defined with respect to certain anatomical landmarks. The location of each defined plane within the data set is computed from the determined locations of the anatomical landmarks. Any portion of the skin surface determined in stage 36 that lies within a region delineated by the defined planes can then be categorized as corresponding to a sensitive area of the patient.

In other embodiments, the processing unit 26 uses a definition of each skin surface region that comprises a central point and a radius distance. The processing unit 26 determines the central point on the image data set, and determines a skin surface region, for example, by determining a region of the skin surface that is within the radius of the central point (the radius being measured along the skin surface), or by projecting a circle of the given radius on to the skin surface.

In alternative embodiments, any suitable method may be used to determine each skin surface region. Such methods may be substituted for, or added to, the methods described in stages 34 to 38 above. Any anatomical regions may be determined, for example, landmarks, organs or bones. In some embodiments, an anatomical ontology is used to reference anatomical regions. In some embodiments, at least part of the image data set is registered to an anatomical atlas.

The skin surface region corresponding to each sensitive area may be of any appropriate size and shape. For example, in one embodiment, each skin surface region comprises a circle around the relevant sensitive area, while in another embodiment each skin surface region has a size and shape representative of the area of the skin surface that would be covered by underwear.

In the present embodiment, the processing unit 26 has a predetermined set of sensitive areas, for each of which a skin surface region is determined. In the present embodiment, the predetermined set of sensitive areas comprises breast, pelvis and genital areas. At stage 38, the processing unit determines skin surface regions corresponding to breast, pelvis and genital areas.

In some embodiments, a user (for example, a clinician) makes a selection of which sensitive areas are relevant, from a list of sensitive areas. The selection may comprise all the sensitive areas on the list, or a subset of the sensitive areas on the list. In some embodiments, only selected sensitive areas are determined at stage 38, and sensitive areas that were not selected by the user are not determined at stage 38. In other embodiments, the entire list of available sensitive areas are determined at stage 38, but only those selected by the user are modified or obscured as described below with reference to stage 38.

In some embodiments, more than one predetermined set of sensitive areas is stored by the processing unit 26. For example, in an embodiment, different sets of sensitive areas are stored for each gender.

At stage 40, the processing unit 26 determines whether any of the predetermined set of sensitive areas will be shown in the requested image when rendered and displayed. If the requested rendered image does not include any sensitive areas (for example, in the present embodiment, the requested rendered image is a view of the patient's arm only) then the processing unit 26 renders the requested image using the skin surface preset. If any of the predetermined set of sensitive areas will be present in the requested image, the processing unit proceeds to stage 42.

In alternative embodiments in which individual rendering parameters are used instead of or in addition to a preset, the processing unit 26 determines whether the selected parameter settings are skin-revealing. If the selected rendering parameters are not skin-revealing, the processing unit 26 renders the requested image using the selected rendering parameters. If the selected rendering parameters are skin-revealing, the processing unit 26 determines whether the requested rendered image will show sensitive areas. If the selected rendering parameters are skin-revealing, but no sensitive areas will be present, the processing unit 26 renders the requested image using the selected rendering parameters. If the selected rendering parameters are skin-revealing and the rendered image will reveal sensitive areas, the processing unit proceeds to stage 42.

At stage 42, the processing unit 26 renders from the image data set an image of the patient in which each of the skin surface regions determined in stage 36 has its appearance modified, or is obscured, by applying a visual effect to the skin surface region itself, or to an area near or covering the skin surface region. In the present embodiment, the remainder of the skin surface (parts of the skin surface that are not within the skin surface regions determined at stage 38) is rendered without modification or obscuration. In other embodiments, areas of modification or obscuration may extend beyond the determined skin surface regions. For example, an area between two skin surface regions may be modified or obscured such that one area of modification or obscuration covers both skin surface regions.

The processing unit 26 displays the rendered image to the user on display screen 16.

In the present embodiment, the visual effect applied to the skin surface regions which correspond to the sensitive areas is pixelation. Pixelation of a skin surface region (alternatively called pixelization) refers to rendering the skin surface region such that the skin surface region is displayed as a small number of large pixels, thus obscuring the detail in the skin surface region. Pixelation of a skin surface region may comprise in some cases rendering the skin surface region at considerably reduced resolution. In the present embodiment, the pixelation effect in the image appears to be applied conformal to the skin surface, i.e. the pixelated part of the body retains its overall shape and curvature, although with a reduction in detail.

In alternative embodiments, the visual effect comprises rendering the image such that a two-dimensional pixelated shape (for example, a circle or a square) appears to be placed over the skin surface region. For example, a pixelated square may appear over the genital region.

In some embodiments, at stage 38, instead of determining a skin surface region for each sensitive area, the processing unit 26 determines a point corresponding to the center of the sensitive area. A two-dimensional pixelated shape is rendered that is centered on the point.

In further embodiments, each skin surface region corresponding to a sensitive area is obscured by rendering the image such that an opaque shape (for example, a black square) appears to be placed over the skin surface region. In other embodiments, any method of masking the skin surface regions in the image may be used.

In alternative embodiments, the visual effect comprises smoothing the part of the image corresponding to the skin surface region (for example applying to each pixel of the image a filter that averages the values of the surrounding pixels) or reducing the resolution of the part of the image corresponding to the skin surface region. In further embodiments, the part of the image corresponding to the skin surface region may be distorted using any appropriate distortion method. In other embodiments, a layer of voxels outside the body are rendered as skin voxels, such that detail of the actual skin surface is obscured. The layer of voxels may be a layer that is at least several voxels in thickness.

In some embodiments, the processing unit 26 renders an image in which the sensitive areas appear to be covered, for example by fabric. In some such embodiments, the fabric is rendered such that details in the skin surface are smoothed out or otherwise concealed (the fabric does not appear to be skin-tight).

In some embodiments, the processing unit 26 renders an image in which the sensitive areas appear to be covered by clothing, for example by underwear (this may be referred to as virtual clothing or digital underwear).

In some such embodiments, a representation of a solid object (which may be described as digital underwear) is added to the image data set such that the solid object appears adjacent to the skin surface. The digital underwear replaces the air, clothing or couch voxels that were originally present next to the skin. The digital underwear has a similar Hounsfield value to skin. Voxels in the digital underwear may have the same intensities as typical or neighboring skin voxels.

In some embodiments, the digital underwear is generated from a template. The processing unit 26 registers the template to the actual skin surface, for example using non-rigid registration.

The HU values of the digital underwear may be selected at random according to a distribution taken from the sensitive skin area. Noise may be added to the HU values of voxels of the digital underwear. Selecting the HU values at random and/or adding noise to the HU values may avoid the possibility of it being possible to readily sculpt away the digital underwear. For example, it may be possible to sculpt away the digital underwear if it is known that the digital underwear has a particular fixed HU value.

By reducing the Hounsfield gradient at the boundary between the skin surface and the digital underwear, it may become impossible to generate photorealistic image from the modified data set that look like a naked body.

In some embodiments, the sensitive areas are defined to include any part of the body that may be covered by the applied clothing. In other embodiments, the sensitive areas are defined more narrowly, and further areas of skin surface are defined to correspond to areas of clothing. The further areas may be a predetermined set of clothing regions.

In one embodiment, several predetermined sets of clothing regions are defined in processing unit 26. Each set of clothing regions corresponds to a different level of body coverage. For example, where the sensitive area is the pelvis, the corresponding clothing region in one set of clothing regions comprises brief underwear, whereas the corresponding clothing region in another set of clothing regions comprises knee-length shorts. A user may select which clothing regions to use, or a clothing region preference may be set in an imaging system (for example, dependent on which country the system is installed in) and the clothing regions applied automatically. In some embodiments, the appearance of the clothing may be realistic. Clothing may be selected (manually or automatically) from a library of gender-specific or culture-specific clothing types associated with body parts.

In some embodiments, the skin surface regions are rendered using a first value for a rendering parameter and the remainder of the skin surface is rendered using a second, different value for the rendering parameter. In one embodiment, the part of the skin surface that does not correspond to any of the skin surface regions is rendered with a skin surface preset, but the skin surface regions are rendered with a non-skin surface preset, for example with a sub-skin-surface preset. Therefore, the skin surface regions are modified to show subcutaneous features instead of skin features, while skin is shown on the rest of the body.

In further embodiments, skin surface regions corresponding to sensitive areas of the skin surface are replaced with corresponding regions from a different data set, for example with corresponding regions from a virtual anatomy model. For example, the face of the patient in the image may be replaced by a generic face from a virtual anatomy. The region from the virtual anatomy may be registered to the image data set.

In further embodiments, any method of modifying the appearance of, or obscuring, part or all of the skin surface may be used. Modifying or obscuring part of the skin surface may be referred to as veiling that part of the skin surface.

The process of modification or obscuration applied by the processing unit 26 may use any appropriate method of processing the image data set and/or any appropriate method of rendering the image data set. For example, in some embodiments, the processing unit 26 first edits the image data set, for example using methods described with reference to the embodiment of FIG. 4 below. The processing unit 26 then renders the image data set in a conventional manner. In some embodiments, the processing unit 26 edits the image data set without regard to whether sensitive areas will be shown in a particular rendered image.

In other embodiments, the processing unit 26 does not make a change to the image data set, but uses different rendering parameters than would be used to render an image in which all sensitive areas are shown.

In the present embodiment, sensitive areas are rendered using pixelation by default, and no other form of modification or obscuration is used. In other embodiments, alternative forms of modification or obscuration are available. In some embodiments, a user, for example a clinician, can select the type of modification or obscuration to be used. For example, in one embodiment, the user can choose whether to pixelate the skin surface regions corresponding to the sensitive areas or to place an opaque shape over the sensitive areas. In another embodiment, the user can choose whether to distort the skin surface regions corresponding to the sensitive areas or to apply clothing to the skin surface regions corresponding to the sensitive areas. In a further embodiment, the user can decide which form of clothing to apply to the sensitive areas.

In the present embodiment, the image that is initially displayed on display screen 16 is an image in which the skin surface regions corresponding to a predetermined list of sensitive areas are modified or obscured. At stage 44, a user (for example, a clinician) may decide to un-modify or un-obscure one (or more) of the sensitive areas, thus displaying an image in which that sensitive area is shown without modification or obscuration, but in which any other sensitive areas are still modified or obscured. If the user wishes to reveal one of the sensitive areas, the user enters a reveal command using an input device 18. In the present embodiment, the user clicks on the sensitive area to be revealed with a mouse. In other embodiments, the user presses a button, uses a keyboard command, enters a text command, presses a touch screen, gives a voice command or provides any other suitable input.

At stage 46, the processing unit 26 renders and displays an image in which the user-selected sensitive area is un-modified and un-obscured (but in which any other sensitive areas remain modified/obscured).

In the present embodiment, the processing unit 26 renders the image in which the user-selected area is un-modified and un-obscured in response to the user's reveal command. However, in other embodiments, un-modified and un-obscured images are rendered along with the modified/obscured image, but are only displayed if or when requested by the reveal command.

In the present embodiment, if the user wishes to reveal more than one sensitive area, the user selects each of the sensitive areas individually by clicking with the mouse on each of the sensitive areas. In alternative embodiments, a reveal-all command is provided. Use of the reveal-all command displays an image in which all of the sensitive areas in the image are shown as un-modified and un-obscured.

By using reveal or reveal-all commands, modified or obscured skin surface regions may be restored to an un-modified and un-obscured state.

In an alternative embodiment, a user uses an input device 18 (for example, a mouse or trackball) to select a modified/obscured area of the original image which the user wishes to reveal. For example, by clicking and dragging a mouse, the user selects a rectangular region of the original image which includes at least part of at least one modified/obscured area. Any part of any modified or obscured area that is included in the rectangular region is then shown as non-modified and non-obscured, while modified or obscured areas outside the selected rectangular region remain modified or obscured.

In alternative embodiments, sensitive areas may be revealed by different methods. Any suitable reveal or reveal-all command or region selection may be used as described above. Alternatively or additionally, performing specific actions with relation to the displayed (modified/obscured) image, for example manipulating the image, may cause sensitive areas to be revealed in un-modified/un-obscured form.

For example, in some embodiments, the image that is initially displayed to the user has skin surface regions corresponding to a predetermined list of sensitive areas modified or obscured. However, when the user zooms in on a sensitive area, the sensitive area is shown as un-modified/un-obscured.

For example, in an embodiment, the body is displayed with sensitive areas obscured by default, for example in a full body view in which virtual clothing is applied to sensitive areas. Sensitive areas are revealed only as necessary on zooming into a region of interest that comprises a sensitive area.

In a further embodiment, an un-modified/un-obscured image is displayed while the image is being manipulated (for example, rotated or panned) but the corresponding modified/obscured image is displayed while the image is idle.

By displaying sensitive areas only in response to a user command or action, embodiments may avoid incidental viewing of sensitive areas when viewing such areas is not medically required.

In another embodiment, a central portion of an image is displayed un-modified/un-obscured while the remainder of the image has sensitive areas modified/obscured. For example, on a rotating 3D image, the region that appears nearest to the user is un-modified/un-obscured.

In an embodiment, multiple images are displayed on a single display screen. For example, a region of interest is viewed using a variety of concurrently displayed views of the region, for example views in different planes or of different image types. The selection of the views for display and the order and relative positioning of the views is specified by a hanging protocol. A number of image panes contain images each of a predefined type and order. On initial display, all sensitive areas are modified/obscured in each of the image panes.

The user may select one image pane as the active view, for example by positioning a mouse pointer or other indicator over that image pane. When the user selects an image pane as the active view, the image in the selected pane is displayed with all of the sensitive areas un-modified and un-obscured, while images in other panes still have sensitive areas modified or obscured. By showing only the active image in full, it may be possible to limit the display of sensitive areas only to when the image is being actively used, avoiding unnecessary display.

In the following discussion, references to un-modified/un-obscured images refer to images comprising sensitive areas, in which are least one sensitive area is shown un-modified and un-obscured.

In some embodiments, un-modified/un-obscured images revert to modified/obscured images after a period of inaction. For example, if no actions have been performed relating to the image for a period of 5 minutes, any image in which any sensitive area is un-modified/un-obscured reverts to the equivalent image in which all sensitive areas are modified/obscured.

In the present embodiment, using a reveal or reveal-all command or performing an action that will display an un-modified/un-obscured image results directly in the un-modified/un-obscured image being displayed. However, in further embodiments, a further input is required from the user at stage 44 before displaying the un-modified/un-obscured image at stage 46. For example, in some embodiments, if the user inputs a reveal command (for example, by entering a text command or by clicking on the area of the image representing a sensitive area), the processing unit 26 displays a dialog box with a request for confirmation. The user is required to input a confirmation before the un-modified/un-obscured image is shown. For example, a dialog box displays the message 'Do you really need to see this image?' and the user clicks a 'Yes' button to proceed to the un-modified/un-obscured image.

In some embodiments, user requests for un-modified/un-obscured images may be recorded, for example on the patient's file. A record may be kept of each user who accesses a particular un-obscured/un-modified image. A record may be kept of the image views that a particular user requests. Requests for un-modified/un-obscured images may be subsequently audited.

In some embodiments, if the user requests an un-modified/un-obscured image, the processing unit 26 displays a request for the user to enter login details, a password, an encryption key or other similar detail, or to swipe a pass or ID card. The processing unit 26 displays the un-modified/un-obscured image only after the user replies in an acceptable manner, for example with the correct encryption key. If an incorrect input is provided by the user, the processing unit 26 displays a message that indicates that permission is denied, and continues to display the modified/obscured image.

Although various user confirmations are described above, in the present embodiment, user confirmation is only requested in the case where the image includes sensitive areas, and therefore the first image shown to the user is modified/obscured. If the first image is determined at stage 40 to not include any sensitive areas, then the first image shown to the user will not have any areas modified or obscured, and therefore the user will not have any need to request areas of the image to be revealed.

In some embodiments, only certain users or classes of users are allowed to view un-modified/un-obscured images which comprise sensitive areas. In some such embodiments, requesting an un-modified/un-obscured image of sensitive areas triggers a request for login details, a password, an ID card, or any other indication of the user's identity, status, security permissions or profile.

In other embodiments, HIPAA or other privacy regulations may restrict access to authorized personnel, and therefore an authentication step may have been required before any viewing of images is commenced. If an authentication step has previously been performed, the user has already been authenticated and their roles and privileges are already known. Therefore, when the user requests an un-modified/un-obscured image, the processing unit 26 may use the stored authentication details from the user.

If the user is found to be a user who is allowed to view the un-modified/un-obscured image, then the un-modified/un-obscured image is displayed. If the user's input indicates that the user is not allowed to view the un-modified/un-obscured image, the processing unit 26 displays a message that indicates that permission is denied, and continues to display the modified/obscured image. The attempt to access the un-modified/un-obscured image by the user may be recorded.

In some embodiments, only a named referring physician and a named radiologist may view un-obscured/un-modified images of a particular patient.

In some embodiments, some classes of user can view un-modified/un-obscured images of all patients, some classes of user can view un-modified/un-obscured images only of particular patients and/or some classes of user are not allowed to view un-modified/un-obscured images of any patient.

For example, in a teaching hospital, a patient may be asked whether they give consent for students to view images on their file in un-obscured/un-modified form. In such a case, qualified doctors may be allowed to view un-obscured/un-modified images of all patients but students may be allowed to view un-obscured/un-modified images of patients only in the cases where the patient has given permission.

Classes of user may be based on the role, specialism or level of seniority of the user (for example, classes of user may include non-medic, student, radiographer, referring physician and radiologist), or may be based on any other information about the user. In some embodiments, information about a user is stored in a user profile, and when the user provides login details after requesting a non-modified/non-obscured image, the processing unit 26 determines from the user profile whether the user should be given permission to view the image, for example by querying the user's role. In some embodiments, the user's profile includes details of which un-modified/un-obscured images the user is permitted to view. Classes of user may depend on the department of the user. For example, there may be no restrictions of image viewing within radiology, but more restrictions for enterprise users (for example referring physicians or surgeons).

In some embodiments, the user logs in before starting a viewing session. When the user requests an un-modified/un-obscured image, the processing unit 24 determines whether the user is allowed to view the image by querying the user's profile. In some embodiments, some users are allowed to reveal the un-modified/un-obscured image without any further confirmation, whereas other users receive a request for confirmation (for example, a request to re-enter their password). For example, in some embodiments, radiographers, referring physicians and radiologists may be allowed to use the reveal tool without entering a password, students may be required to enter a password every time they use the reveal tool, and non-medics may be prevented from viewing non-modified/non-obscured images.

In some embodiments, a reveal tool is disabled or not present when the user is not allowed to view un-modified/un-obscured images.

Any suitable criteria or method may be used to limit access to non-modified/non-obscured images.

In the embodiment of FIG. 2, the image in which sensitive areas are modified or obscured is shown first to the user by default, and the user can only view an image in which sensitive areas are un-modified/un-obscured by entering a reveal command or performing an action that elicits the un-modified/un-obscured image.

In some embodiments, the display of images to some users may default to an un-modified/un-obscured view, while the display of images to other users defaults to a modified/obscured view. For example, more senior users may have un-modified/un-obscured views displayed by default, while more junior users may see modified/obscured images by default and may be required to use a reveal tool to view un-modified/un-obscured images.

In some embodiments, whether a modified/obscured image or non-modified/non-obscured image is displayed by default may be dependent on a viewing context or hanging protocol. For example, in a radiological reading context, all images may be shown as non-modified/non-obscured. In a multi-disciplinary consultation or a consultation with the patient or their family, sensitive areas in the image may be modified/obscured by default, but the clinician may be able to reveal the sensitive areas. In education or training, only the modified/obscured image may be available.

In some embodiments, whether un-modified/un-obscured images may be viewed may depend on the software or hardware used to view the images. In some embodiments, the viewing may depend on the device used. For example, workstations used for radiology may display un-modified/un-obscured images by default, while tablet computers used by doctors may display modified/obscured images by default.

In some embodiments, whether sensitive areas of images are modified or obscured may depend on an explicit or an assumed patient preference. For example, patient consent may be required (for example, via a consent form) if un-modified/un-obscured images are to be shown. The patient's cultural or religious background may be taken into account. In some embodiments, default settings are used that relate to the country in which the images are being viewed. Different countries may use different lists of sensitive areas, or may differ in whether the default image view is non-modified/non-obscured (with the ability to modify/obscure on patient request) or whether the default image view is modified/obscured (with the ability to reveal in circumstances in which viewing the sensitive areas is necessary, or in which patient consent has been given).

In some embodiments, the access to un-modified/un-obscured images depends on whether the case has been reported or not. When reporting, no restrictions are applied but after reporting restrictions are applied to guard against non-essential use.

In some embodiments, the use of a modified or obscured view of sensitive areas is an optional feature or mode of certain hardware or software (which may be referred to as a modesty view). In some embodiments, the user may choose when to apply the modified or obscured view. In other embodiments, the modified or obscured view is controlled by, for example, how the software or hardware is configured on installation, or by restrictions applied by the institution (for example, hospital) in which the software or hardware is used. In some embodiments, the use of a modified or obscured view is an optional feature used only in particular situations, for example when consulting with a patient or the patient's family, or when training students.

Any appropriate criteria may be used to determine access to non-obscured/non-modified images or availability of a reveal tool, or to determine which image (modified/obscured or non-modified/non-obscured) is shown by default.

Embodiments above have been described in terms of first displaying a modified/obscured image, and applying a reveal tool to obtain a non-modified/non-obscured version of the same image. However, embodiments also exist in which a user views a non-modified/non-obscured image and applies a cover tool or other appropriate method or command to obtain a modified/obscured version of the image. For example, a physician viewing the non-modified/non-obscured image on a display screen may change the image to a modified/obscured image before turning the display screen towards the patient.

In the embodiment of FIG. 2, skin surface regions corresponding to sensitive areas are determined in the image data set by locating anatomical landmarks and the skin surface in the image data set. In further embodiments, skin surface regions are determined by first deriving a two-dimensional image data set from the volumetric techniques and then determining skin surface regions in the two-dimensional image data set. The two-dimensional image data set may be representative of an image of the patient (which may be a quasi-three-dimensional image).

Skin surface regions are determined in the two-dimensional image data set by using any suitable image processing technique.

In one embodiment, the processing unit 26 uses face recognition software to detect whether a face is present in the two-dimensional image data set. If a face is present, the face recognition software determines the location of the face and the extent of the face. The processing unit 26 modifies the appearance of, or obscures, the face within the two-dimensional image data, for example by pixelation or masking, and displays the resulting modified or obscured image. Any suitable method of modifying or obscuring the face may be used. In other embodiments, pattern recognition or shape recognition may be used to detect any sensitive area in the two-dimensional image data.

Figure 4:
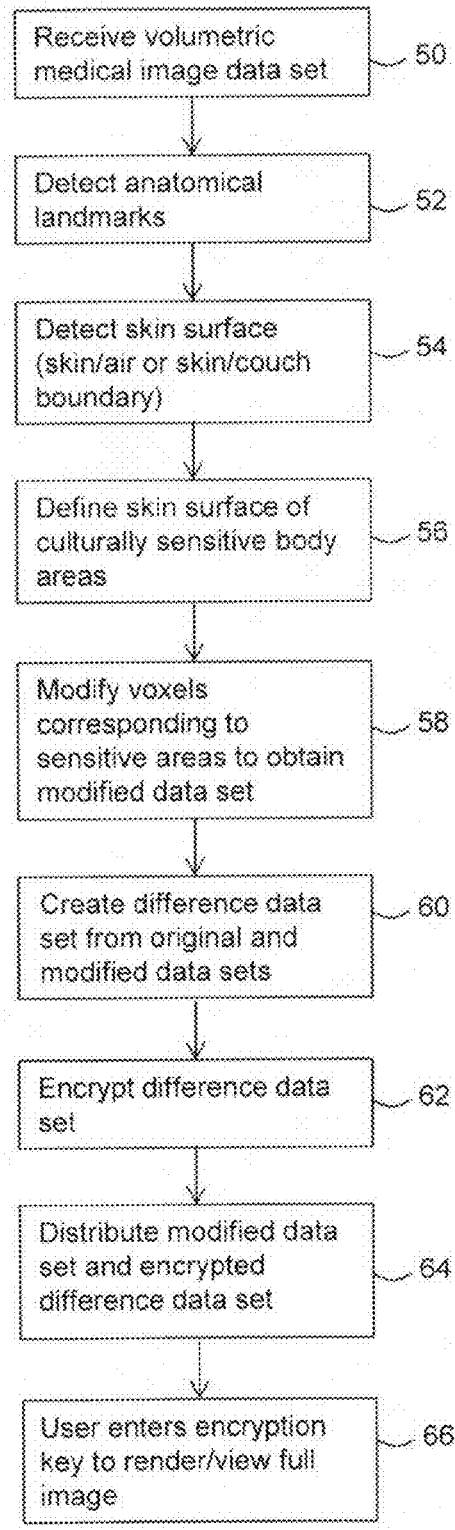
FIG. 4 is a flowchart illustrating in overview a mode of operation of an embodiment.

A further embodiment capable of being performed by the system of FIG. 1 is illustrated in the flow chart of FIG. 4, in which parts of an image data set that correspond to sensitive areas are modified, and access to the original version of the modified areas is restricted by encryption.

Stages 50 to 56 of the process of FIG. 4 correspond to stages 30, 34, 36 and 38 of the process of FIG. 2. At stage 50, the data receiving unit 24 receives a set of volumetric medical image data. At stage 52, the processing unit 26 detects anatomical landmarks within the image data set, or loads positions of anatomical landmarks. At stage 54, the processing unit 26 detects the skin surface of the patient as represented in the image data set by finding the skin/couch and/or skin/air boundaries. At stage 56, the processing unit uses the anatomical landmarks determined in stage 52 and the skin surface determined in stage 54 to determine skin surface regions corresponding to a predetermined list of sensitive areas. In the present embodiment, the sensitive areas are breast, pelvis and genitals. However, in other embodiments skin surface regions corresponding to any one or more sensitive areas may be determined. For example, in one embodiment, only the skin surface region corresponding to the face is determined. In another embodiment, all of the skin surface except the hands and feet is considered to be sensitive. The processing unit 26 determines a subset of image data set that corresponds to the sensitive areas of the image data set.

At stage 58 of the present embodiment, the processing unit 26 modifies the voxels of the subset of the image data set corresponding to the selected sensitive areas and stores a resulting data set (the modified data set), while retaining the image data set that was originally received by the data receiving unit (the original data set).

In the present embodiment, digital underwear is added adjacent to the skin surface by registering a digital underwear template to the image data set. The HU values of the digital underwear are selected at random from a distribution of skin voxels for the actual skin surface.

In other embodiments, any method may be used in which a layer of voxels adjacent to the skin surface (which may be several voxels thick) is modified to obtain the modified data set. Each voxel in the layer of voxels may be set to an intensity representative of skin. The layer of voxels may be calculated such that, when the image data set is rendered, a thick layer of what appears to be skin will conceal details of the patient's skin surface.

In other embodiments, skin voxels in a skin surface region are modified by setting the intensity of the skin voxels to the intensity of air, or setting the skin voxels to null or to padding (removing the skin voxels). In such embodiments, the skin in the skin surface region may become invisible in an image rendered from the image data set.

In further embodiments, voxels of the image data set may be modified using any method that will result in an image rendered from the image data set having the sensitive areas modified or obscured. For example, dither may be added to the voxels, or voxel values may be averaged over a local neighborhood.

In some embodiments, voxels may be modified before a diagnostic read of the image data had been performed. In other embodiments, voxels may be modified only after the diagnostic read. Voxels may be modified before using the data as a training or conference case.

In the present embodiment, the modifying of voxels does not depend on whether a particular view of the image data set has been requested, but only depends on whether sensitive areas are present in the image data set, whether or not those sensitive areas would be shown in a particular image render.

At stage 60, the processing unit 26 creates a difference data set, where the difference data set represents the difference between the original data set and the modified data set. At stage 62, the processing unit 26 encrypts the difference data set to restrict access to the difference data set. At stage 64 of the embodiment of FIG. 4, the modified data set and encrypted difference data set are distributed to one or more users.

In the present embodiment, a user who receives or accesses the modified data set is able to create images from the modified data set without requiring an encryption key. The modified data set may be used to create images in which the sensitive areas are modified or obscured, but is not, by itself, capable of being used to create images in which sensitive areas are un-modified and un-obscured. If the modified data set is used to create images in which no sensitive areas are present, the same image will be obtained from the modified data set as would be obtained from the original data set. Only sensitive areas are modified.

At stage 66, a user wishes to create an image in which at least one of the sensitive areas is un-modified and un-obscured. To create an image in which any of the sensitive areas is un-modified and un-obscured, the user must have the modified data set and encrypted difference data set, and must enter an encryption key to de-encrypt the difference data set. The modified data set and encrypted difference data set may then be combined to render and view an un-modified and un-obscured image.

In some embodiments, only the modified data set is distributed to users. In other embodiments, both the modified data set and the difference data set are distributed to users, and users who are allowed to access the un-modified and un-obscured images are provided with the encryption key required to decrypt the difference data set.

In particular embodiments, only the modified data set may be kept by the processing unit 26 after stage 58, and the original data set in which the sensitive areas are represented may be discarded. However, it may be more likely that the both the modified data set and the difference data set or, equivalently, the modified data set and original data set are stored (for example on the patient's file) but restrictions are placed on the distribution of the difference data set or original data set.

For example, in one embodiment, the sensitive area is the face. When data is to be distributed to be used in education, training or research, for which anonymity is required, only the modified data set is distributed. It is not possible to view the face using the modified data set, so the patient's privacy is protected. The inability to view the face is intrinsic to the modified data set and cannot be overcome by, for example, using different software, settings or permissions.

In further embodiments, the modified data set and an encrypted version of the original data set are distributed. A user can render and view an image from the modified data set. In the resulting image, sensitive areas are modified or obscured. To render and view an image in which sensitive areas are visible, the user is required to decrypt the original data set and render the image from the original data set rather than from the modified data set.

In some embodiments, access to both the modified data set and the difference data set (or original data set) is restricted but with different levels of security. For example, in one embodiment accessing the modified data set requires a password, while accessing the difference data set (or original data set) requires both a password and an encryption key).

In some embodiments, the difference data set or original data set may be retrieved if using suitably configured software.

Viewing software or hardware may restrict access to images in similar ways to those described with relation to the embodiment of FIG. 2. For example, to render an image using the difference data set or original data set, the user may have to be of an allowed class of users, as well as having the required encryption key.

In some embodiments, the modification of the image data file is restorable given correct security privileges. For example, the image data file may be restorable given a private DICOM tag.

In some embodiments, the process of FIG. 4 is performed in an image processing apparatus 10 that is separate from the scanner 14. In other embodiments, the process of FIG. 4 is performed within the scanner 14 on image capture, or in equipment integrated with the scanner 14. For example, if the scanner 14 captures an image that includes sensitive areas, then the image data set may be modified before leaving the scanner 14.

In some embodiments, modification of voxels in the image data set takes place only when the image data set is leaving the normal jurisdiction, for example entering a training set or being otherwise distributed outside the hospital.

In some embodiments, image data is distributed locked to some viewing software. For example, image data may be distributed as a keepsake or take-home scan, or for educational or training purposes. In such cases, the viewing software may be configured to apply any of the methods of modification or obscuration described in any of the above embodiments. A standard set of hide/obscure mechanisms may be provided, or a set of hide/obscure mechanisms may be applied by a user in preparation for creating the distributable data.

In the embodiments of FIG. 2 and FIG. 4, limited regions of the skin surface are selected, these selected regions corresponding to sensitive areas (culturally sensitive or patient-identifying areas). In further embodiments, the entire skin surface of the patient is considered to be sensitive, and therefore visualization of any part of the skin surface of the patient is restricted.

In one such embodiment, access to a skin surface preset, or to any set of rendering parameters that reveals the skin, is restricted. When a user requests an image view that requires a skin surface preset (or skin-revealing rendering parameters), the user has to provide, for example, a password or encryption key before such an image is rendered and/or displayed. In some embodiments, every request for an image using a skin surface preset (or skin-revealing rendering parameters) is recorded.

In some embodiments, use of the skin surface preset (or skin-revealing rendering parameters) is restricted in dependence on the identity or role of the user. For example, radiologists may use a skin surface preset without restrictions, but the use of the skin surface preset by students requires a password and is recorded. In this embodiment, restriction of the use of the skin surface preset applies to all areas, not just those in which particular sensitive areas are displayed.

In another embodiment, access to images of the skin surface is restricted by modifying voxels in the image data set such that all voxels in a volume exterior to the patient (for example, air or couch voxels) are set to an intensity that is representative of tissue, for example skin tissue, thereby flood-filling the image so that the skin surface cannot be displayed. Voxels in the flood-filled area may be set to similar intensities to typical or neighboring skin voxels. Noise may be added to the flood-filled area to avoid the flood-fill being removed by a seed and sculpt operation that targets a particular HU value.

In 3D rendering, a transfer function renders different Hounsfield units as different opacities. In a normal rendering, skin tissue (or any soft tissue) is rendered as reasonably opaque, while air voxels are rendered with low opacity.

The embodiments described above are performed on patient data. The patient referred to in the above embodiments may be any human subject. The patient may or may not necessarily be a patient of the hospital in which the patient is scanned to acquire the image data set, or of the doctor who has ordered the scan. The patient may be healthy. The patient may be a medical study participant. The patient may be a cadaver on which forensic imaging is being performed.

Any of the embodiments above may be integrated in a radiological product. The radiological product may be a software product (for example, visualization software) or a hardware product (for example, a scanner or a radiological workstation).

Although the embodiments above have been described with reference to CT imaging and Hounsfield units, similar methods may also be applied to MR images. Appropriate changes may be made to MR data sets, for example to MR voxel values.

Skin surface rendering, including rendering of sensitive areas, may be clinically required. It may be important that a clinician's ability to view the skin surface when necessary is not significantly or unnecessarily impaired. However, by using the embodiments described herein it may be possible to avoid unnecessary on-screen display of sensitive areas, the display of which may raise privacy or modesty concerns. By using embodiments described herein, visualization of sensitive areas may be restricted to users, or classes of users, who have a plausible genuine need to display images of such sensitive areas. The display of sensitive areas may be restricted (in space and/or in time) to the minimum required to fulfill any task that must be performed.

In, for example, the embodiments of FIG. 2 and FIG. 4, by accurately detecting the skin surface and anatomical landmarks, the unnecessary display of images of culturally sensitive body parts may be restricted. Similarly, the unnecessary display of patient-identifying images may be restricted.

For some patient groups, a hospital that uses one or more of the above embodiments may provide patients with a feeling of greater privacy and of being treated with greater respect. Hospitals may use such embodiments as part of a commitment to preserving patient dignity. The above embodiments may be of particular value in specific countries in which higher levels of modesty concerns are prevalent.

By using the above embodiments, a hospital can claim tight control over who views images comprising sensitive areas. A hospital can audit viewing of images that comprise sensitive areas. Controls can be applied (for example, by modifying the image data set) before an image data set even leaves the scanner and enters general distribution within the hospital.

Certain embodiments provide a method of radiological image display, comprising loading a volumetric image data set of a human subject, detecting anatomical regions within the data set, detecting the skin surface within the data set, and displaying the data set such that the skin surface of selected anatomical regions is modified or obscured.

In some embodiments, the modifying or obscuring of the selected regions is conditional on any combinations of a zoom level, a reveal tool, a user profile, a hanging protocol or a patient profile.

Certain embodiments provide a method of radiological image storage, comprising acquiring a volumetric image data set of a human subject, detecting anatomical regions within the data set, detecting the skin surface within the data set, modifying the intensity values of a layer of voxels adjacent to the skin surface and/or including the skin surface of selected anatomical regions, and storing the data set as modified. The layer of voxels may comprise a layer that is several voxels in thickness. In some embodiments, a means to restore modified voxels to their previous state is provided.

In some embodiments, the detected anatomical regions are chosen from the set including face, breast, pelvis and genitals. In some embodiments, detecting anatomical regions within the data set is accomplished with reference to detected anatomical landmarks. In some embodiments, detecting anatomical regions within the data set is accomplished using face recognition, shape recognition or pattern recognition on an image derived from the volumetric image data set. In some embodiments, detecting anatomical regions within the data set is accomplished with reference to an anatomical ontology. In some embodiments, detecting anatomical regions within the data set is accomplished by registering the data set to a generic anatomical atlas comprising real or virtual anatomical data.

Although particular embodiments have been described above, features of any embodiment may be combined with features of any other embodiment.

Whilst particular units have been described herein, in alternative embodiments functionality of one or more of these units can be provided by a single unit, processing resource or other component, or functionality provided by a single unit can be provided by two or more units or other components in combination. Reference to a single unit encompasses multiple components providing the functionality of that unit, whether or not such components are remote from one another, and reference to multiple units encompasses a single component providing the functionality of those units.

Whilst certain embodiments have been described, these embodiments have been presented by way of example only, and are not intended to limit the scope of the invention. Indeed the novel methods and systems described herein may be embodied in a variety of other forms; furthermore, various omissions, substitutions and changes in the form of the methods and systems described herein may be made without departing from the spirit of the invention. The accompanying claims and their equivalents are intended to cover such forms and modifications as would fall within the scope of the invention.

The invention claimed is:

1. An image processing apparatus, comprising:
processing circuitry configured to:
receive a volumetric medical image data set, the medical image data set being representative of internal anatomy of a patient;
process the volumetric medical image data set to detect voxels representative of the skin surface; and
restrict visualization of at least part of the detected voxels representative of the patient's skin surface,
wherein the processing circuitry is further configured to:
detect and localize a plurality of anatomical landmarks in the volumetric medical image data set,
detect the patient's skin surface by at least one of finding a boundary between skin and an object which contacts the patient's body and finding a boundary between the skin and air, and
determine a part of the patient's skin surface based on the anatomical landmarks and the patient's skin surface, and
wherein the determined part of the patient's skin surface is restricted from visualization.

2. An apparatus according to claim 1, wherein processing the volumetric medical image data set surface comprises restricting access to a rendering setting.

3. An apparatus according to claim 1, wherein processing the medical image data set comprises determining at least one anatomical region in the medical image data set, wherein determining the or each anatomical region comprises at least one of a), b) and c):
a) determining the location of at least one anatomical landmark in the medical image data set;
b) referencing an anatomical ontology; and
c) registering at least part of the medical image data set to an anatomical atlas.

4. An apparatus according to claim 3, wherein processing the medical image data further comprises relating the or each anatomical region to at least one skin surface region.

5. An image processing method, comprising:
using processing circuitry to receive a volumetric medical image data set, the volumetric medical image data set being representative of internal anatomy of a patient; and
processing the medical image data using the processing circuitry set to restrict visualization of at least part of the patient's skin surface
wherein processing the medical image data includes:
detecting and localizing a plurality of anatomical landmarks in the volumetric medical image data set,
detecting the patient's skin surface by at least one of finding a boundary between skin and a couch which contacts the patient's body and finding a boundary between the skin and air, and
determining a part of the patient's skin surface based on the anatomical landmarks and the patient's skin surface, and
restricting the determined part of the patient's skin surface from visualization.

6. An image processing method, comprising:
using processing circuitry to receive a volumetric medical image data set, the volumetric medical image data set being representative of at least part of a patient; and
processing the medical image data using the processing circuitry set to restrict visualization of at least part of the patient's skin surface by one of applying virtual clothing or virtual anatomy.

7. An image processing apparatus, comprising:
processing circuitry configured to:
receive a volumetric medical image data set, the medical image data set being representative of at an internal anatomy of a patient;
process the volumetric medical image data set to detect voxels representative of the skin surface; and
restrict visualization of at least part of the detected voxels representative of the patient's skin surface by one of applying virtual clothing and applying virtual anatomy.

8. An apparatus according to claim 7, wherein the processing circuitry is configured to process the volumetric medical image data set by modifying the appearance of, or obscuring, at least one skin surface region.

9. An apparatus according to claim 8, wherein the processing circuitry is further configured to process the volumetric medical image data set by determining the or each skin surface region to be modified or obscured.

10. An apparatus according to claim 9, wherein modifying the appearance of or obscuring, the or each determined skin surface region comprises rendering at least one of the or each determined skin surface region, wherein the or each skin surface region is rendered with a first value for a rendering parameter, and at least one further skin surface region is rendered with a second, different rendering parameter.

11. An apparatus according to claim 9, wherein modifying the appearance of, or obscuring, the or each determined skin surface region comprises rendering the or each skin surface region with a non-skin surface preset and rendering at least one further skin surface region with a skin surface preset.

12. An apparatus according to claim 9, wherein the processing circuitry is further configured to display, in dependence on a user input, an image in which the or each determined skin surface region is non-modified and non-obscured.

13. An apparatus according to claim 9, wherein processing the medical image data set further comprises:
processing the medical image data set to obtain two-dimensional image data representative of a two-dimensional image; and
determining the or each determined skin surface region in the two-dimensional image data.

14. An apparatus according to claim 13, wherein determining the or each determined skin surface region in the two-dimensional image data comprises at least one of face recognition, shape recognition and pattern recognition.

15. An apparatus according to claim 7, wherein processing the medical image data set comprises processing the medical image data set in order to restrict access to at least part of the medical image data set.

16. An apparatus according to claim 15, wherein processing the medical image data set in order to restrict access to at least part of the medical image data set comprises determining a subset of the medical image data set, the subset comprising data corresponding to at least one skin surface region, and restricting access to the subset.

17. An apparatus according to claim 16, wherein restricting access to the subset comprises at least one of a) and b):
a) storing the subset separately to another part of the medical image data set; and
b) modifying voxels in the subset.

18. An apparatus according to claim 15, wherein restricting access to at least part of the medical image data set comprises at least one of a), b), c) and d):
   a) encrypting at least part of the medical image data set;
   b) password-protecting at least part of the medical image data set;
   c) applying a security setting to at least part of the medical image data set; and
   d) restricting access to at least part of the medical image data set in dependence on at least one of a user profile, a patient profile, a hanging protocol, a processing device, a display device, a location, a display program, a rendering program.

19. An apparatus according to claim 15, wherein processing the medical image data set comprises determining whether at least one skin surface region is present in the medical image data set, and wherein access to at least part of the medical image data set is restricted in dependence on the determination of whether the or each skin surface region is present.

\* \* \* \* \*